United States Patent [19]

Yang et al.

[11] Patent Number: 4,468,476

[45] Date of Patent: Aug. 28, 1984

[54] COLOR PRECURSOR REMOVAL FROM DETERGENT ALKYL BENZENES

[75] Inventors: Kang Yang; James D. Reedy, both of Ponca City, Okla.

[73] Assignee: Conoco Inc., Ponca City, Okla.

[21] Appl. No.: 556,678

[22] Filed: Jan. 3, 1984

Related U.S. Application Data

[63] Continuation-in-part of Ser. No. 392,431, Jun. 25, 1982, Pat. No. 4,433,196.

[51] Int. Cl.$^3$ ............................................... B01J 20/08
[52] U.S. Cl. ...................................... 502/83; 208/260; 210/690; 210/917; 585/823
[58] Field of Search ...................... 502/83, 84, 85, 414, 502/74, 80, 81, 415; 585/820, 823; 208/260; 210/679, 690, 917

[56] References Cited

U.S. PATENT DOCUMENTS

| | | | |
|---|---|---|---|
| 2,118,310 | 5/1938 | Kauffman | 502/80 |
| 2,346,127 | 4/1944 | Simpson et al. | 502/80 |
| 3,835,037 | 9/1974 | Fairweather et al. | 208/260 |
| 4,229,612 | 10/1980 | Hall, Jr. et al. | 585/823 |
| 4,243,831 | 1/1981 | Malloy et al. | 585/820 |
| 4,247,729 | 1/1981 | Takahashi et al. | 585/823 |
| 4,423,278 | 12/1983 | Yang et al. | 585/823 |
| 4,433,196 | 2/1984 | Yang et al. | |

Primary Examiner—Delbert E. Gantz
Assistant Examiner—Anthony McFarlane
Attorney, Agent, or Firm—Robin M. Davis; Cortlan R. Schupbach

[57] ABSTRACT

An adsorbent is provided for removing color precursors from detergent range alkyl benzene prior to sulfonation. The adsorbent provided is a bauxite clay having at least one material selected from the group consisting of ferric oxide, titanium dioxide, and zirconium oxide and which contain from about 0.1 to about 20 percent by weight of sulfuric acid, said bauxite clay then being calcined at a temperature and time sufficient to activate the adsorbent prior to use.

3 Claims, No Drawings

COLOR PRECURSOR REMOVAL FROM DETERGENT ALKYL BENZENES

BACKGROUND AND FIELD OF THE INVENTION

This application is a continuation-in-part of my prior application Ser. No. 392,431, filed June 25, 1982, for Color Precursor Removal From Detergent Range Alkyl Benzenes now U.S. Pat. No. 4,433,196.

Detergent range alkyl benzenes can be made substantially free of color precursors which would cause color after sulfonation. The present invention provides for an adsorbent capable of removing color precursors from detergent range alkyl benzenes before sulfonation.

The alkylation of aromatic hydrocarbons, in particular benzene, has long been practiced as a step in the manufacture of alkyl aryl sulfonate detergents. The alkylated aromatic hydrocarbons, generally alkyl benzene, are subsequently sulfonated and neutralized to give the desired salt of the alkyl aryl sulfonic acid, which constitutes the active detergent material. The prior art recognizes that the true mixture of unreacted components, alkylated aromatics, high molecular weight compounds, catalysts, and hydrogen chloride called alkylate (obtained from the alkylation process) requires purification if high quality detergents are to be produced and certain processing problems are to be avoided.

The prior art also recognizes that the sulfonation of alkyl aryl hydrocarbons has generally followed a procedure wherein sulfuric acid is used to sulfonate the alkyl aryl hydrocarbons. The resultant sulfonic acid yields a dark colored sulfonate when neutralized with a base such as sodium hydroxide. These colored sulfonates are useful only in a relatively few applications, and it is therefore desirable to remove color bodies imparting color to the sulfonate. The adsorbent herein described has the capacity for removing bodies which would cause color in sulfonated alkyl benzene from alkyl benzenes prior to sulfonation.

The prior art does contain descriptions of methods employing various substances which are used to purify aromatic hydrocarbons. U.S. Pat. No. 3,835,037 teaches that adsorbents for aromatic streams can be derived from clay material having acidic sites. This patent further describes clay treatment stages to remove objectionable color generating impurities. U.S. Pat. No. 2,778,863 describes a process for removing diolefins from aromatic distillates using a clay treating unit in which a mild clay treatment is used.

However, methods such as these are not entirely satisfactory. The products obtained from such treatment have not been improved greatly in color and in many cases the resulting improvement is only temporary. Furthermore, naturally occuring clay is noticeably not as affective for removing color from sulfonated alkyl aryl hydrocarbons.

It is an object of the instant invention to provide an adsorbent capable of removing color precursors from alkyl aryl hydrocarbons prior to sulfonation. The adsorbent described in the instant invention is noticeably improved over the naturally found bauxite clay.

BRIEF DESCRIPTION OF THE INVENTION

An adsorbent for removing from alkyl benzene, precurors which cause color in sulfonated alkyl benzene comprises: bauxite clay containing from about 0.1 to about 20 percent by weight of at least one material selected from a group consisting of iron oxides, titanium dioxide, and zirconium oxide; sulfuric acid added to the bauxite clay in an amount of from about 0.1 to about 20 percent by weight of sulfuric acid based on the total weight of the adsorbent; wherein the clay and sulfuric acid mixture is calcined at a temperature and for a time sufficient to activate the adsorbent prior to use.

The adsorbent of the present invention removes certain polyaromatic impurities causing color in sulfonated alkyl benzene. These precursors can be removed in a fixed bed process using this sulfuric acid treated and subsequently calcined clay. This material is most effective for detergent range alkyl benzenes containing high 2-phenyl isomer content (generally above about 20 percent by weight); these are currently manufactured by the aluminum chloride alkylation of benzene with alkyl chloride. The resulting feedstock contains some polyaromatic impurities causing color problems in the subsequent sulfonation step.

The sulfuric acid and bauxite clay adsorbent of the instant invention is capable of removing color precursors from alkyl benzenes so that the alkyl benzene feed has an acceptable absorbence spetrophotometrically. Generally the absorbence of an untreated alkyl benzene feed produced from aluminum chloride catalized process is about 0.44. Surfactants with acceptable color are produced when the absorbence of the alkyl benzene is less than 0.06 determined spectrophotometrically as absorbence at 368 nanometers (nm wave length). The capacity of this adsorbent is about ten volumes of alkyl benzene which before treatment has an absorption of about 0.44, per one volume of adsorbent.

DETAILED DESCRIPTION OF THE INVENTION

The clay adsorbent of the present invention is a bauxite clay containing at least one material selected from the group consisting of ferric oxide, titanium dioxide, and zirconium oxide. This clay is activated for effective precursor adsorption by mixing with sulfuric acid and then calcining the mixture at a temperature and time sufficient to activate the adsorbent prior to use.

Normally the adsorbent will contain from about one to about 20 percent by weight of ferric oxide based on the total weight of the bauxite clay, and from about 0.1 to about 20 percent by weight of titanium dioxide and from about 0.1 to about 20 percent by weight zirconium oxide, all based on the total weight of the bauxite clay. Within these ranges the clay is found to be an effective adsorbent. It is, however, preferred that the clay contain from about 0.2 to about 12 percent by weight of these materials.

The clay thus described is then mixed with sulfuric acid. The sulfuric acid used can be either concentrated or diluted, but the clay must contain from about 0.1 to about 20 percent by weight sulfuric acid. The most preferred amount of sulfuric acid is from about 0.5 to about 15 percent by weight based on the total weight of the adsorbent.

After mixing the sulfuric acid with the bauxite clay, the mixture is calcined at a temperature and time sufficient to activate the adsorbent for color precursor removal. Time and temperature of this activation will vary considerably, but normally the calcination is carried out at a temperature from about 300° C. to about 700° C. The preferred temperature range is from about 500° to about 600° C. The time of calcination is a time sufficient to make the catalyst efficient in removing the color precursors. This time can vary widely and is not critical other than being sufficient for activation to occur.

Bauxite clays useful in the practice of the present invention are found occuring in nature. Many clays with the composition described can be utilized. Representative but nonexhaustive examples of the bauxite clays useful in the present invention are Milwhit percolation grade (10 to 30 mesh) bauxite clays (trademark of and sold by the Milwhit Co., Inc., Houston, Tex.).

Utilizing the adsorbent of the present invention in removing color precursors from alkyl benzene prior to sulfonation, the alkyl benzene is contacted with the adsorbent for a time sufficient to remove the precursor. The present invention is best utilized by passing the alkyl benzene through the adsorbent at a liquid hourly space velocity of from about 0.1 to about 10. A liquid hourly space velocity (LHSV) of from about 0.5 to about 5 is preferred, and an LHSV of from about 1 to about 4 is most preferred.

The adsorbent of the instant invention is suitable for use at any convenient temperature. Normally room temperature is satisfactory.

Pressure or lack of pressure is not detrimental to the present invention, and the adsorption can be carried out at any convenient pressure, whether above or below ambient.

The invention is more concretely described with reference to the examples below wherein all parts and percentages are by weight unless otherwise specified. The examples are provided to illustrate the instant invention and not to limit it.

The adsorbent of the instant invention was prepared and compared to a commercially available bauxite clay sold by Milwhit Co. Inc.

EXAMPLE 1

A bauxite adsorbent of the present invention was prepared by sulfuric acid impregnation of clay and subsequent calcination. The clay used was Milwhit percolation grade bauxite (trademark of and sold by The Milwhit Co. Inc., 10/30 mesh) having from 75 to 78 weight percent alumina, from 8 to 16 weight percent ferric oxide, from 7 to 9 percent silica, 4 weight percent titanium dioxide, and from 6 to 7 percent volatile matter. One hundred grams of this clay was mixed with 20 grams of concentrated sulfuric acid. The mixture was evaporated to dryness on a rotary evaporator, and calcined in atmospheric air at 550° C. for 15 hours. The resulting adsorbent was packed into a one half inch stainless steel tube having a 12 cubic centimeter (cc) volume and an adsorption run was made at room temperature and a LHSV of 2.5.

The above prepared adsorbent was compared to another batch of percolation grade bauxite (Milwhit Co. Inc., 10/30 mesh) of comparible content. This clay was similarly calcined in atmospheric air at 550° C. for 15 hours and that adsorbent was similarly introduced into a one half inch stainless steel tube having a 12 cubic centimeter (cc) volume and an adsorption attempt was made at room temperature and a liquid hourly space velocity of 2.5.

The alkyl benzene feed used in each adsorption run was produced by alkylating with a linear alkyl chloride having from about 10 to about 14 carbon atoms with benzene using an aluminum chloride catalyst. The concentration of the color precursor was determined using a spectrophotometer and absorption at 368 nanometers wave length. After absorption over the bauxite clay, and the adsorbent of the instant invention, the alkyl benzene was again checked at 368 nanometers for absorption. The results are set forth in Table 1 below.

TABLE 1

| Adsorption untreated feed was 0.44 heat activated bauxite clay and $H_2SO_4$. ||
| --- | --- |
| Time (Hr.) | Absorbence |
| 0-1 | 0.024 |
| 1-2 | 0.041 |
| 2-3 | 0.053 |
| 3-4 | 0.061 |

The capacity of the instant adsorbent is about 10 volumes of alkyl benzene having a .44 absorbence at 368 nm per volume of adsorbent.

| Heat activated bauxite clay ||
| --- | --- |
| Time | Absorbence |
| 0-1 | 0.44 |

While certain embodiments and details have been shown for the purpose of illustrating this invention, it will be apparent to those skilled in this art that various changes and modifications may be made herein without departing from the spirit or scope of the invention.

We claim:

1. An adsorbent for removing from alkyl benzene, the precursors which cause color in sulfonated alkyl benzene comprising:
   bauxite clay containing from about 0.1 to about 20 percent by weight of at last one material selected from a group consisting of iron oxides, titanium dioxide, and zirconium oxide; sulfuric acid added to the bauxite clay in an amount of from about 0.7 to about 20 percent by weight of sulfuric acid based on the total weight of the adsorbent; wherein the clay and sulfuric acid mixture is calcined at a temperature for a time sufficient to activate the adsorbent prior to use.

2. An adsorbent as described in claim 1 wherein from about 0.2 to about 12 percent of iron oxides, titanium dioxide and zirconium oxide is in the bauxite clay.

3. An adsorbent as described in claim 2 wherein sulfuric acid is in the amount of from about 0.5 to about 15 percent by weight of the bauxite clay.

* * * * *